(12) United States Patent  
Burgermeister et al.

(10) Patent No.: US 7,794,493 B2
(45) Date of Patent: Sep. 14, 2010

(54) MAGNETIC RESONANCE IMAGING COMPATIBILITY ALLOY FOR IMPLANTABLE MEDICAL DEVICES

(75) Inventors: Robert Burgermeister, Bridgewater, NJ (US); Volker Niermann, Bound Brook, NJ (US); Yuchen Qiu, Belle Mead, NJ (US); Theresa Scheuble, Rockaway, NJ (US)

(73) Assignee: Cordis Corporation, Miami Lakes, FL (US)

( * ) Notice: Subject to any disclaimer, the term of this patent is extended or adjusted under 35 U.S.C. 154(b) by 1424 days.

(21) Appl. No.: 10/881,424

(22) Filed: Jun. 30, 2004

(65) Prior Publication Data

US 2006/0004435 A1 Jan. 5, 2006

(51) Int. Cl.
*A61F 2/06* (2006.01)
(52) U.S. Cl. .................................... 623/1.34
(58) Field of Classification Search ......... 606/191–198; 623/1.1–1.22, 23.69, 23.7
See application file for complete search history.

(56) References Cited

U.S. PATENT DOCUMENTS

| 4,733,665 | A | 3/1988 | Palmaz |
| 5,044,368 | A | 9/1991 | Putz et al. |
| 5,632,771 | A | 5/1997 | Boatman et al. |
| 5,725,572 | A | 3/1998 | Lam et al. |
| 5,733,326 | A * | 3/1998 | Tomonto et al. ........... 623/1.44 |
| 5,741,327 | A | 4/1998 | Frantzen |
| 5,800,526 | A | 9/1998 | Anderson et al. |
| 6,022,374 | A | 2/2000 | Imran |
| 7,250,058 | B1 * | 7/2007 | Pacetti et al. ................ 606/198 |
| 2002/0058989 | A1 | 5/2002 | Chen et al. |
| 2002/0123795 | A1 | 9/2002 | Jalisi |

FOREIGN PATENT DOCUMENTS

| EP | 0804934 A | 11/1997 |
| EP | 1 604 619 B1 | 3/2008 |
| WO | WO 01/72349 A | 10/2001 |

OTHER PUBLICATIONS

European Search Report EP 05 25 3862 dated Nov. 15, 2005.
Communication Pursuant to Article 96(2) EPC for Application 05 253 862.6 - 1219, Applicant Cordis Corporation, dated Aug. 22, 2007, by Menidjel, Razik, Primary Examiner for the Examining Division, pp. 1-4.

* cited by examiner

*Primary Examiner*—Kevin T Truong

(57) ABSTRACT

A biocompatible solid-solution alloy may be formed into any number of implantable medical devices. The solid-solution alloy comprises a combination of elements in specific ratios that make it magnetic resonance imaging compatible while retaining the characteristics required for implantable medical devices. The biocompatible solid-solution alloy is a cobalt-chromium alloy having substantially reduced iron, silicon, phosphorus and sulfur content.

14 Claims, 6 Drawing Sheets

MAGNETIC RESONANCE IMAGING COMPATIBILITY ALLOY FOR IMPLANTABLE MEDICAL DEVICES

BACKGROUND OF THE INVENTION

1. Field of the Invention

The present invention relates to alloys for use in manufacturing or fabricating implantable medical devices, and more particularly, to implantable medical devices manufactured or fabricated from alloys that are magnetic resonance imaging compatible.

2. Discussion of the Related Art

Percutaneous transluminal angioplasty (PTA) is a therapeutic medical procedure used to increase blood flow through an artery. In this procedure, the angioplasty balloon is inflated within the stenosed vessel, or body passageway, in order to shear and disrupt the wall components of the vessel to obtain an enlarged lumen. With respect to arterial stenosed lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue, which may reduce the blood flow through the lumen, or completely block the lumen. Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct the problem.

Recently, transluminal prostheses have been widely used in the medical arts for implantation in blood vessels, biliary ducts, ureters, or other similar organs of the living body. These prostheses are commonly referred to as stents and are used to maintain, open, or dilate tubular structures. An example of a commonly used stent is given in U.S. Pat. No. 4,733,665 to Palmaz. Such stents are often referred to as balloon expandable stents. Typically the stent is made from a solid tube of stainless steel. Thereafter, a series of cuts are made in the wall of the stent. The stent has a first smaller diameter, which permits the stent to be delivered through the human vasculature by being crimped onto a balloon catheter. The stent also has a second, expanded diameter, upon application of a radially, outwardly directed force, by the balloon catheter, from the interior of the tubular shaped member.

However, one concern with such stents is that they are often impractical for use in some vessels such as the carotid artery. The carotid artery is easily accessible from the exterior of the human body, and is close to the surface of the skin. A patient having a balloon expandable stent made from stainless steel or the like, placed in their carotid artery, might be susceptible to severe injury through day-to-day activity. A sufficient force placed on the patient's neck could cause the stent to collapse, resulting in injury to the patient. In order to prevent this, self-expanding stents have been proposed for use in such vessels. Self-expanding stents act like springs and will recover to their expanded or implanted configuration after being crushed.

The prior art makes reference to the use of alloys such as Nitinol (Ni—Ti alloy), which have shape memory and/or superelastic characteristics, in medical devices, which are designed to be inserted into a patient's body, for example, self-expanding stents. The shape memory characteristics allow the devices to be deformed to facilitate their insertion into a body lumen or cavity and then be heated within the body so that the device returns to its original shape. Superelastic characteristics, on the other hand, generally allow the metal to be deformed and restrained in the deformed condition to facilitate the insertion of the medical device containing the metal into a patient's body, with such deformation causing the phase transformation. Once within the body lumen, the restraint on the superelastic member can be removed, thereby reducing the stress therein so that the superelastic member can return to its original un-deformed shape by the transformation back to the original phase.

One concern with self-expanding stents and with other medical devices formed from superelastic materials, is that they may exhibit reduced radiopacity under X-ray fluoroscopy. To overcome this problem, it is common practice to attach markers, made from highly radiopaque materials, to the stent, or to use radiopaque materials in plating or coating processes. Those materials typically include gold, platinum, or tantalum. The prior art makes reference to these markers or processes in U.S. Pat. No. 5,632,771 to Boatman et al., U.S. Pat. No. 6,022,374 to Imran, U.S. Pat. No. 5,741,327 to Frantzen, U.S. Pat. No. 5,725,572 to Lam et al., and U.S. Pat. No. 5,800,526 to Anderson et al. However, due to the size of the markers and the relative position of the materials forming the markers in the galvanic series versus the position of the base metal of the stent in the galvanic series, there is a certain challenge to overcome; namely, that of galvanic corrosion. Also, the size of the markers increases the overall profile of the stent. In addition, typical markers are not integral to the stent and thus may interfere with the overall performance of the stent as well as become dislodged from the stent.

A concern with both balloon expandable and self-expandable stents is magnetic resonance imaging compatibility. Currently available metallic stents are known to cause artifacts in magnetic resonance generated images. In general, metals having a high magnetic permeability cause artifacts, while metals having a low magnetic permeability cause less or substantially no artifacts. In other words, if the stent or other medical device is fabricated from a metal or metals having a low magnetic permeability, then less artifacts are created during magnetic resonance imaging, which in turn allows more tissue in proximity to the stent or other medical device to be imaged.

Artifacts created under magnetic resonance imaging are promoted by local magnetic field inhomogeneities and eddy currents induced by the magnetic field generated by the magnetic resonance imaging machine. The strength of the magnetic field disruption is proportional to the magnetic permeability of the metallic stent or other medical device. In addition, signal attenuation within the stent is caused by radio frequency shielding of the metallic stent or other medical device material. Essentially, the radio frequency signals generated by the magnetic resonance imaging machine may become trapped within the cage like structure of the stent or other medical device. Induced eddy currents in the stent may also lead to a lower nominal radio frequency excitation angle inside the stent. This has been shown to attenuate the signal acquired by the receiver coil of the magnetic resonance imaging device. Artifact related signal changes may include signal voids or local signal enhancements, which in turn degrades the diagnostic value of the tool.

Accordingly, there is a need to develop materials for implantable medical devices, such as stents, that are magnetic resonance imaging compatible while retaining the toughness, durability and ductility properties required of implantable medical devices such as stents.

SUMMARY OF THE INVENTION

The present invention overcomes the diagnostic tool limitations associated with currently available implantable medical devices as briefly described above.

In accordance with one aspect, the present invention is directed to an implantable medical device being formed from an improved, magnetic resonance compatible solid-solution alloy. The solid solution alloy comprises chromium in the range from about 19 weight percent to about 21 weight percent, tungsten in the range from about 14 weight percent to about 16 weight percent, nickel in the range from about 9 weight percent to about 11 weight percent, manganese in the range from about 1 weight percent to about 2 weight percent, carbon in the range from about 0.05 weight percent to about 0.15 weight percent, iron in an amount not to exceed 0.3 weight percent, silicon in an amount not to exceed 0.4 weight percent, phosphorus in an amount not to exceed 0.04 weight percent, sulfur in an amount not to exceed 0.03 weight percent and the remainder cobalt.

In accordance with another aspect, the present invention is directed to a biocompatible, load-carrying metallic structure being formed from an improved, magnetic resonance compatible solid solution alloy. The solid solution alloy comprises chromium in the range from about 19 weight percent to about 21 weight percent, tungsten in the range from about 14 weight percent to about 16 weight percent, nickel in the range from about 9 weight percent to about 11 weight percent, manganese in the range from about 1 weight percent to about 2 weight percent, carbon in the range from about 0.05 weight percent to about 0.15 weight percent, iron in an amount not to exceed 0.3 weight percent, silicon in an amount not to exceed 0.4 weight percent, phosphorus in an amount not to exceed 0.04 weight percent, sulfur in an amount not to exceed 0.03 weight percent and the remainder cobalt.

The biocompatible alloy for implantable medical devices of the present invention offers a number of advantages over currently utilized alloys. The biocompatible alloy of the present invention is magnetic resonance imaging compatible, is less brittle than other alloys, has enhanced ductility and toughness, and has increased durability. The biocompatible alloy also maintains the desired or beneficial characteristics of currently available alloys including strength and flexibility.

The magnetic resonance imaging compatibility of implantable medical devices is gaining interest for the guidance of endovascular interventional procedures and post-treatment evaluation. The magnetic resonance imaging compatibility of the material or materials forming the medical devices is related to the basic magnetic susceptibility of the materials relative to human tissue. A number of elements are ferromagnetic, including iron, cobalt and nickel; however, iron has a magnetic susceptibility multiple orders of magnitude greater than these other elements. Accordingly, reducing the iron content in an alloy substantially reduces the magnetic susceptibility of the alloy, thereby enhancing magnetic resonance imaging.

The biocompatible alloy for implantable medical devices of the present invention may be utilized for any number of medical applications, including vessel patency devices such as vascular stents, biliary stents, ureter stents, vessel occlusion devices such as atrial septal and ventricular septal occluders, patent foramen ovale occluders and orthopedic devices such as fixation devices. In addition, the biocompatible alloy may be utilized in the construction of delivery devices for various medical devices. For example, the alloy may be utilized in the fabrication of guidewires.

The biocompatible alloy of the present invention is simple and inexpensive to manufacture. The biocompatible alloy may be formed into any number of structures or devices. The biocompatible alloy may be thermomechanically processed, including cold-working and heat treating, to achieve varying degrees of strength and ductility. The biocompatible alloy of the present invention may be age hardened to precipitate one or more secondary phases.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
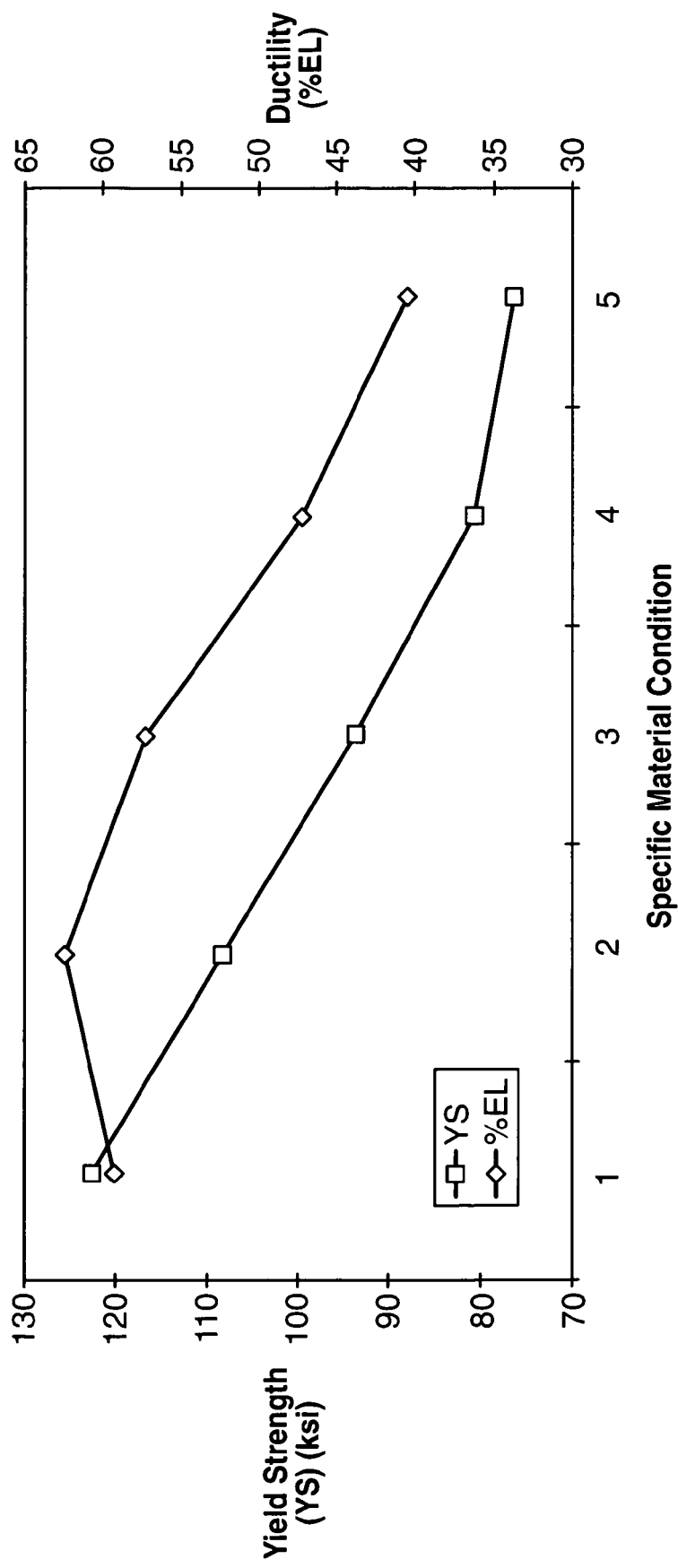
FIG. 1 is a graphical representation of the transition of critical mechanical properties as a function of thermomechanical processing for cobalt-chromium alloys in accordance with the present invention.

Biocompatible, solid-solution alloys may be utilized in the manufacture of any number of implantable medical devices. The biocompatible alloy for implantable medical devices in accordance with the present invention offers a number of advantages over currently utilized medical grade alloys. In particular, the biocompatible alloy of the present invention is magnetic resonance imaging compatible. Magnetic resonance imaging is a valuable diagnostic tool and thus any implantable medical device should preferably be magnetic resonance imaging compatible so that it and surrounding tissue may be accurately imaged. One such medical device where this is particularly relevant is stents.

Coronary stenting is currently the most widely utilized percutaneous coronary intervention. The primary benefit of stenting when compared with balloon-angioplasty alone is a reduction of the restenosis-rate. Nevertheless, in-stent restenosis remains a relatively common clinical scenario. If clinical symptoms suggest in-stent restenosis, x-ray coronary angiography is currently considered the standard for the evaluation of stent integrity. Conventional x-ray angiography has a number of disadvantages, including a small risk of potentially serious complications, the need for a contrast agent containing a form of iodine, and radiation exposure. Accordingly, a noninvasive imaging method for direct assessment of stent lumen integrity would be preferable. Magnetic resonance imaging provides such a method.

Currently, the majority of coronary artery stents are ferromagnetic but are considered to be magnetic resonance imaging safe. Although these devices are considered magnetic resonance imaging safe, they traditionally induce image artifacts that may pose inaccurate, clinically relevant inferences when inspected by a clinician. For example, traditional biocompatible cobalt-alloys such as L605 (common tradename: Haynes 25 from the Haynes International Corporation) can have as much as 3 wt. % iron. Biocompatible metallic alloys that contain strongly ferromagnetic materials such as iron, but not limited thereto, generally exhibit a high magnetic permeability which tends to induce unintended image artifacts. Moreover, traditional biocompatible ferrous-based alloys such as stainless steel may contain significantly greater concentrations of strongly ferromagnetic materials such as iron.

For reference, a traditional stainless steel alloy such as 316L (i.e. UNS S31603) which is broadly utilized as an implantable, biocompatible device material may comprise chromium (Cr) in the range from about 16 to 18 wt. %, nickel (Ni) in the range from about 10 to 14 wt. %, molybdenum (Mo) in the range from about 2 to 3 wt. %, manganese (Mn) in the range up to 2 wt. %, silicon (Si) in the range up to 1 wt. %, with iron (Fe) comprising the balance (approximately 65 wt. %) of the composition.

Additionally, a traditional cobalt-based alloy such as L605 (i.e. UNS R30605) which is also broadly utilized as an implantable, biocompatible device material may comprise chromium (Cr) in the range from about 19 to 21 wt. %, tungsten (W) in the range from about 14 to 16 wt. %, nickel (Ni) in the range from about 9 to 11 wt. %, iron (Fe) in the range up to 3 wt. %, manganese (Mn) in the range up to 2 wt. %, silicon (Si) in the range up to 1 wt. %, with cobalt (Co) comprising the balance (approximately 49 wt. %) of the composition.

In general, elemental additions such as chromium (Cr), nickel (Ni), tungsten (W), manganese (Mn), silicon (Si) and molybdenum (Mo) where added to iron- and/or cobalt-based alloys, where appropriate, to increase or enable desirable performance attributes, including strength, machinability and corrosion resistance within clinically relevant usage conditions.

The composition of the material of the present invention does not eliminate ferromagnetic components but rather shift the 'susceptibility' (i.e. the magnetic permeability) such that the magnetic resonance imaging compatibility may be improved. In addition, the material of the present invention is intended to improve the measurable ductility by minimizing the deleterious effects induced by traditional machining aides such as silicon (Si).

The traditional cobalt-based alloy, L605, is a nonmagnetic chromium-nickel-tungsten-cobalt alloy. Among the elements comprising the L605 alloy, iron, cobalt and nickel are known ferromagnetic metals. Of these three elements, iron has the highest magnetic susceptibility level. Magnetic susceptibility is a unitless constant that is determined by the physical properties of the material. More particularly, iron has a magnetic susceptibility level of 200,000 in c.g.s. units, cobalt has a magnetic susceptibility level of 250 in c.g.s. units, and nickel has a magnetic susceptibility level of 600 in c.g.s. units. These magnetic susceptibility levels indicate that the iron in the L605 alloy may be the most influential element to the overall L605 alloy's magnetic properties. While the detailed magnetic susceptibility of L605 is unclear, the magnetic rating for L605 is estimated to be within the range between paramagnetic to ferromagnetic.

The iron content in the L605 alloy is a maximum of 3 weight percent. In accordance with an exemplary embodiment, the iron content of the alloy may be reduced to a level of 1 percent or less, and more particularly to a level of less than 0.3 weight percent, with the reduction being covered by an increase in cobalt. The variation in weight percent of iron and cobalt as set forth herein, does not have a measurable impact on material mechanical properties. Accordingly, by controlling the manufacturing process as described herein, it is possible and economically practical to produce an alloy with a significantly reduced iron content, thereby reducing the overall magnetic susceptibility of the alloy.

Figure 6A:
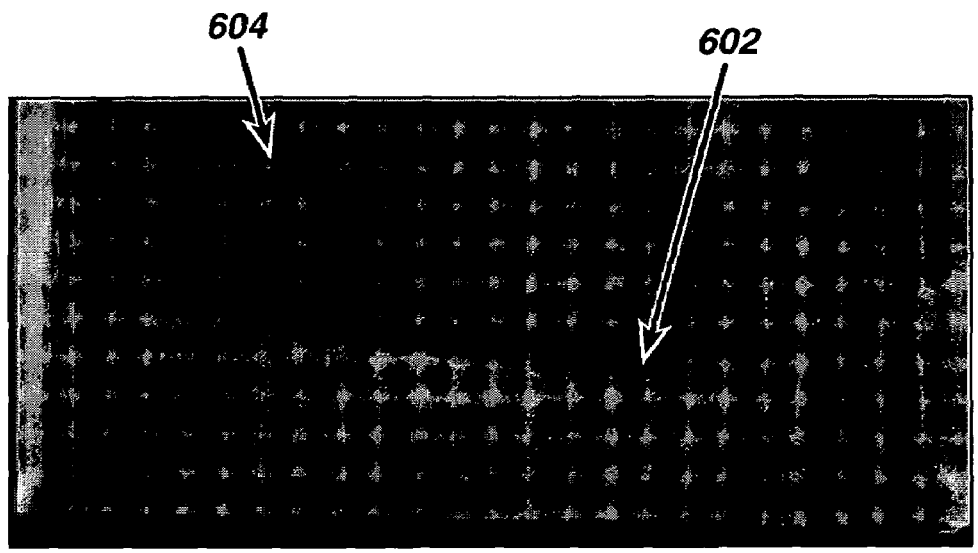
FIGS. 6a and 6b are magnetic resonance images of wires comprising different alloys in a magnetic field in accordance with the present invention.
Figure 6B:
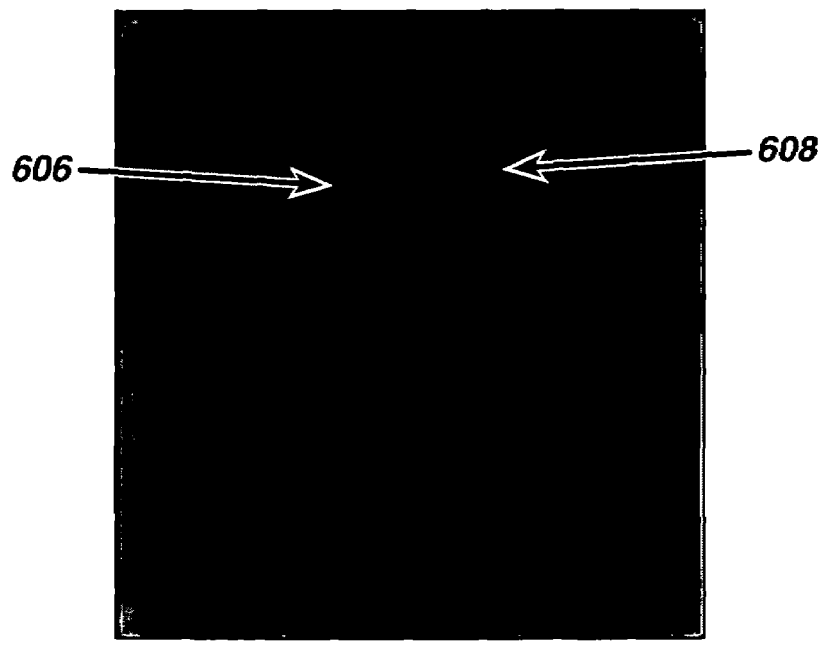

Referring now to FIG. 6a, there is illustrated a magnetic resonance image of two wires positioned such that they are substantially perpendicular to the magnetic field. Wire 602 is a 0.005 inch diameter wire formed from standard L605 (iron content of approximately 2.29 percent by weight). Wire 604 is a 0.005 inch diameter wire formed from the improved alloy (low iron of approximately 0.1 percent by weight) of the present invention. As may be seen from a comparison of the two images, the low iron alloy of the present invention results in a clearer image. In FIG. 6b, the same wires are positioned substantially parallel to the magnetic field. Wire 606, which is formed from standard L605, is blurry, while wire 608 appears substantially invisible. A conclusion based on the two sets of images may be that the low iron alloy of the present invention induces less artifacts and results in better images.

In accordance with an exemplary embodiment, an implantable medical device may be formed from a solid-solution alloy comprising chromium in the range from about 19 weight percent to about 21 weight percent, tungsten in the range from about 14 weight percent to about 16 weight percent, nickel in the range from about 9 weight percent to about 11 weight percent, manganese in the range from about 1 weight percent to about 2 weight percent, carbon in the range from about 0.05 weight percent to about 0.15 weight percent, iron in an amount not to exceed 0.3 weight percent, silicon in an amount not to exceed 0.4 weight percent, phosphorus in an amount not to exceed 0.04 weight percent, sulfur in an amount not to exceed 0.03 weight percent and the remainder cobalt.

In contrast to the traditional formulation of this alloy (i.e. L605/Haynes 25), the intended composition does not include any elemental iron (Fe) or silicon (Si) above conventional accepted trace impurity levels. Accordingly, this exemplary embodiment will exhibit a marked reduction in 'susceptibility' (i.e. the magnetic permeability) thereby leading to improved magnetic resonance imaging compatibility. Additionally, the exemplary embodiment will exhibit a marked improvement in material ductility and fatigue strength (i.e. cyclic endurance limit strength) due to the elimination of silicon (Si), above trace impurity levels.

The preferred embodiment may be processed from the requisite elementary raw materials, as set-forth above, by first mechanical homogenization (i.e. mixing) and then compaction into a green state (i.e. precursory) form. If necessary, appropriate manufacturing aids such as hydrocarbon based lubricants and/or solvents (e.g. mineral oil, machine oils, kerosene, isopropanol and related alcohols) be used to ensure complete mechanical homogenization. Additionally, other processing steps such as ultrasonic agitation of the mixture followed by cold compaction to remove any unnecessary manufacturing aides and to reduce void space within the green state may be utilized. It is preferable to ensure that any impurities within or upon the processing equipment from prior processing and/or system construction (e.g. mixing vessel material, transfer containers, etc.) be sufficiently reduced in order to ensure that the green state form is not unnecessarily contaminated. This may be accomplished by adequate cleaning of the mixing vessel before adding the constituent elements by use of surfactant based cleaners to remove any loosely adherent contaminants.

Initial melting of the green state form into a ingot of desired composition, is achieved by vacuum induction melting (VIM) where the initial form is inductively heated to above the melting point of the primary constituent elements within a refractory crucible and then poured into a secondary mold within a vacuum environment (e.g. typically less than or equal to $10^{-4}$ mmHg). The vacuum process ensures that atmospheric contamination is significantly minimized. Upon solidification of the molten pool, the ingot bar is substantially single phase (i.e. compositionally homogenous) with a definable threshold of secondary phase impurities that are typically ceramic (e.g. carbide, oxide or nitride) in nature. These impurities are typically inherited from the precursor elemental raw materials.

A secondary melting process termed vacuum arc reduction (VAR) is utilized to further reduce the concentration of the secondary phase impurities to a conventionally accepted trace impurity level (i.e. <1,500 ppm). Other methods maybe enabled by those skilled in the art of ingot formulation that substantially embodies this practice of ensuring that atmospheric contamination is minimized. In addition, the initial VAR step may be following followed by repetitive VAR processing to further homogenize the solid-solution alloy in the ingot form. From the initial ingot configuration, the homogenized alloy will be further reduced in product size and form by various industrially accepted methods such as, but not limited too, ingot peeling, grinding, cutting, forging, forming, hot rolling and/or cold finishing processing steps so as to produce bar stock that may be further reduced into a desired raw material form.

In this exemplary embodiment, the initial raw material product form that is required to initiate the thermomechanical processing that will ultimately yield a desired small diameter, thin-walled tube, appropriate for interventional devices, is a modestly sized round bar (e.g. one inch in diameter round bar stock) of predetermined length. In order to facilitate the reduction of the initial bar stock into a much smaller tubing configuration, an initial clearance hole must be placed into the bar stock that runs the length of the product. These tube hollows (i.e. heavy walled tubes) may be created by 'gun-drilling' (i.e. high depth to diameter ratio drilling) the bar stock. Other industrially relevant methods of creating the tube hollows from round bar stock may be utilized by those skilled-in-the-art of tube making.

Consecutive mechanical cold-finishing operations such as drawing through a compressive outer-diameter (OD), precision shaped (i.e. cut), circumferentially complete, diamond die using any of the following internally supported (i.e. inner diameter, ID) methods, but not necessarily limited to these conventional forming methods, such as hard mandrel (i.e. relatively long traveling ID mandrel also referred to as rod draw), floating-plug (i.e. relatively short ID mandrel that 'floats' within the region of the OD compressive die and fixed-plug (i.e. the ID mandrel is 'fixed' to the drawing apparatus where relatively short workpieces are processed) drawing. These process steps are intended to reduce the outer-diameter (OD) and the corresponding wall thickness of the initial tube hollow to the desired dimensions of the finished product.

When necessary, tube sinking (i.e. OD reduction of the workpiece without inducing substantial tube wall reduction) is accomplished by drawing the workpiece through a compressive die without internal support (i.e. no ID mandrel). Conventionally, tube sinking is typically utilized as a final or near-final mechanical processing step to achieve the desired dimensional attributed of the finished product.

Although not practically significant, if the particular compositional formulation will support a single reduction from the initial raw material configuration to the desired dimensions of the finished product, in process heat-treatments will not be necessary. Where necessary to achieve intended mechanical properties of the finished product, a final heat-treating step is utilized.

Conventionally, all metallic alloys in accordance with the present invention will require incremental dimensional reductions from the initial raw material configuration to reach the desired dimensions of the finished product. This processing constraint is due to the material's ability to support a finite degree of induced mechanical damage per processing step without structural failure (e.g. strain-induced fracture, fissures, extensive void formation, etc.).

In order to compensate for induced mechanical damage (i.e. cold-working) during any of the aforementioned cold-finishing steps, periodic thermal heat-treatments are utilized to stress-relieve (i.e. minimization of deleterious internal residual stresses that are the result of processes such as cold-working) thereby increasing the workability (i.e. ability to support additional mechanical damage without measurable failure) the workpiece prior to subsequent reductions. These thermal treatments are typically, but not necessarily limited to, conducted within a relatively inert environment such as an inert gas furnace (e.g. nitrogen, argon, etc.), a oxygen rarified hydrogen furnace, a conventional vacuum furnace and under less common process conditions, atmospheric air. When vacuum furnaces are utilized, the level of vacuum (i.e. subatmospheric pressure), typically measured in units of mmHg or torr (where 1 mmHg is equal to 1 unit torr), shall be sufficient to ensure that excessive and deteriorative high temperature oxidative processes are not functionally operative during heat treatment. This process may usually be achieved under vacuum conditions of $10^{-4}$ mmHg (0.0001 torr) or less (i.e. lower magnitude).

The stress relieving heat treatment temperature is typically held constant between 82 to 86% of the conventional melting point (i.e. industrially accepted liquidus temperature, 0.82 to 0.86 homologous temperatures) within an adequately sized isothermal region of the heat-treating apparatus. The workpiece undergoing thermal treatment is held within the isothermal processing region for a finite period of time that is adequate to ensure that the workpiece has reached a state of thermal equilibrium and for that sufficient time is elapsed to ensure that the reaction kinetics (i.e. time dependent material processes) of stress-relieving and/or process annealing, as appropriate, is adequately completed. The finite amount of time that the workpiece is held within the processing is dependent upon the method of bringing the workpiece into the process chamber and then removing the working upon completion of heat treatment. Typically, this process is accomplished by, but not limited to, use of a conventional conveyor-belt apparatus or other relevant mechanical assist devices. In the case of the former, the conveyor belt speed and appropriate finite dwell-time, as necessary, within the isothermal region is controlled to ensure that sufficient time at temperature is utilized so as to ensure that the process is completed as intended.

When necessary to achieve desired mechanical attributes of the finished product, heat-treatment temperatures and corresponding finite processing times may be intentionally utilized that are not within the typical range of 0.82 to 0.86 homologous temperatures. Various age hardening (i.e. a process that induces a change in properties at moderately elevated temperatures, relative to the conventional melting point, that does not induce a change in overall chemical composition change in the metallic alloy being processed) processing steps may be carried out, as necessary, in a manner consistent with those previously described at temperatures substantially below 0.82 to 0.86 homologous temperature. For Co-based alloys in accordance with the present invention, these processing temperatures may be varied between and inclusive of approximately 0.29 homologous temperature and the aforementioned stress relieving temperature range. The workpiece undergoing thermal treatment is held within the isothermal processing region for a finite period of time that is adequate to ensure that the workpiece has reached a state of thermal equilibrium and for that sufficient time is elapsed to ensure that the reaction kinetics (i.e. time dependent material processes) of age hardening, as appropriate, is adequately completed prior to removal from the processing equipment.

In some cases for Co-based alloys in accordance with the present invention, the formation of secondary-phase ceramic compounds such as carbide, nitride and/or oxides will be induced or promoted by age hardening heat treating. These secondary-phase compounds are typically, but not limited to, for Co-based alloys in accordance with the present invention, carbides which precipitate along thermodynamically favorable regions of the structural crystallographic planes that comprise each grain (i.e. crystallographic entity) that make-up the entire polycrystalline alloy. These secondary-phase carbides can exist along the intergranular boundaries as well as within each granular structure (i.e. intragranular). Under most circumstances for Co-based alloys in accordance with the present invention, the principal secondary phase carbides that are stoichiometrically expected to be present are $M_6C$ where M typically iscobalt (Co). When present, the intermetallic $M_6C$ phase is typically expected to reside intragranularly along thermodynamically favorable regions of the structural crystallographic planes that comprise each grain within the polycrystalline alloy in accordance with the present invention. Although not practically common, the equivalent material phenomena can exist for a single crystal (i.e. monogranular) alloy.

Additionally, another prominent secondary phase carbide can also be induced or promoted as a result of age hardening heat treatments. This phase, when present, is stoichiometrically expected to be $M_{23}C_6$ where M typically is chromium (Cr) but is also commonly observed to be cobalt (Co) especially in Co-based alloys. When present, the intermetallic $M_{23}C_6$ phase is typically expected to reside along the intergranular boundaries (i.e. grain boundaries) within a polycrystalline alloy in accordance with the present invention. As previously discussed for the intermetallic $M_6C$ phase, the equivalent presence of the intermetallic $M_{23}C_6$ phase can exist for a single crystal (i.e. monogranular) alloy, albeit not practically common.

In the case of the intergranular $M_{23}C_6$ phase, this secondary phase is conventionally considered most important, when formed in a manner that is structurally and compositionally compatible with the alloy matrix, to strengthening the grain boundaries to such a degree that intrinsic strength of the grain boundaries and the matrix are adequately balanced. By inducing this equilibrium level of material strength at the microstructural level, the overall mechanical properties of the finished tubular product can be further optimized to desirable levels.

In addition to stress relieving and age hardening related heat-treating steps, solutionizing (i.e. sufficiently high temperature and longer processing time to thermodynamically force one of more alloy constituents to enter into solid solution—'singular phase', also referred to as full annealing) of the workpiece may be utilized. For Co-based alloys in accordance with the present invention, the typical solutionizing temperature can be varied between and inclusive of approximately 0.88 to 0.90 homologous temperatures. The workpiece undergoing thermal treatment is held within the isothermal processing region for a finite period of time that is adequate to ensure that the workpiece has reached a state of thermal equilibrium and for that sufficient time is elapsed to ensure that the reaction kinetics (i.e. time dependent material processes) of solutionizing, as appropriate, is adequately completed prior to removal from the processing equipment.

The sequential and selectively ordered combination of thermomechanical processing steps that may comprise but not necessarily include mechanical cold-finishing operations, stress relieving, age hardening and solutionizing can induce and enable a broad range of measurable mechanical properties as a result of distinct and determinable microstructural attributes. This material phenomena can be observed in FIG. 1. which shows a chart that exhibits the affect of thermomechanical processing (TMP) such as cold working and in-process heat-treatments on measurable mechanical properties such as yield strength and ductility (presented in units of percent elongation) in accordance with the present invention. In this example, thermomechanical (TMP) groups one (1) through five (5) were subjected to varying combinations of cold-finishing, stress relieving and age hardening and not necessarily in the presented sequential order. In general, the principal isothermal age hardening heat treatment applied to each TMP group varied between about 0.74 to 0.78 homologous temperatures for group (1), about 0.76 to 0.80 homologous temperatures for group (2), about 0.78 to 0.82 homologous temperatures for group (3), about 0.80 to 0.84 homologous temperatures for group (4) and about 0.82 to 0.84 homologous temperatures for group (5). The each workpiece undergoing thermal treatment was held within the isothermal processing region for a finite period of time that was adequate to ensure that the workpiece reached a state of thermal equilibrium and to ensure that sufficient time was elapsed to ensure that the reaction kinetics of age hardening was adequately completed.

Figure 2:
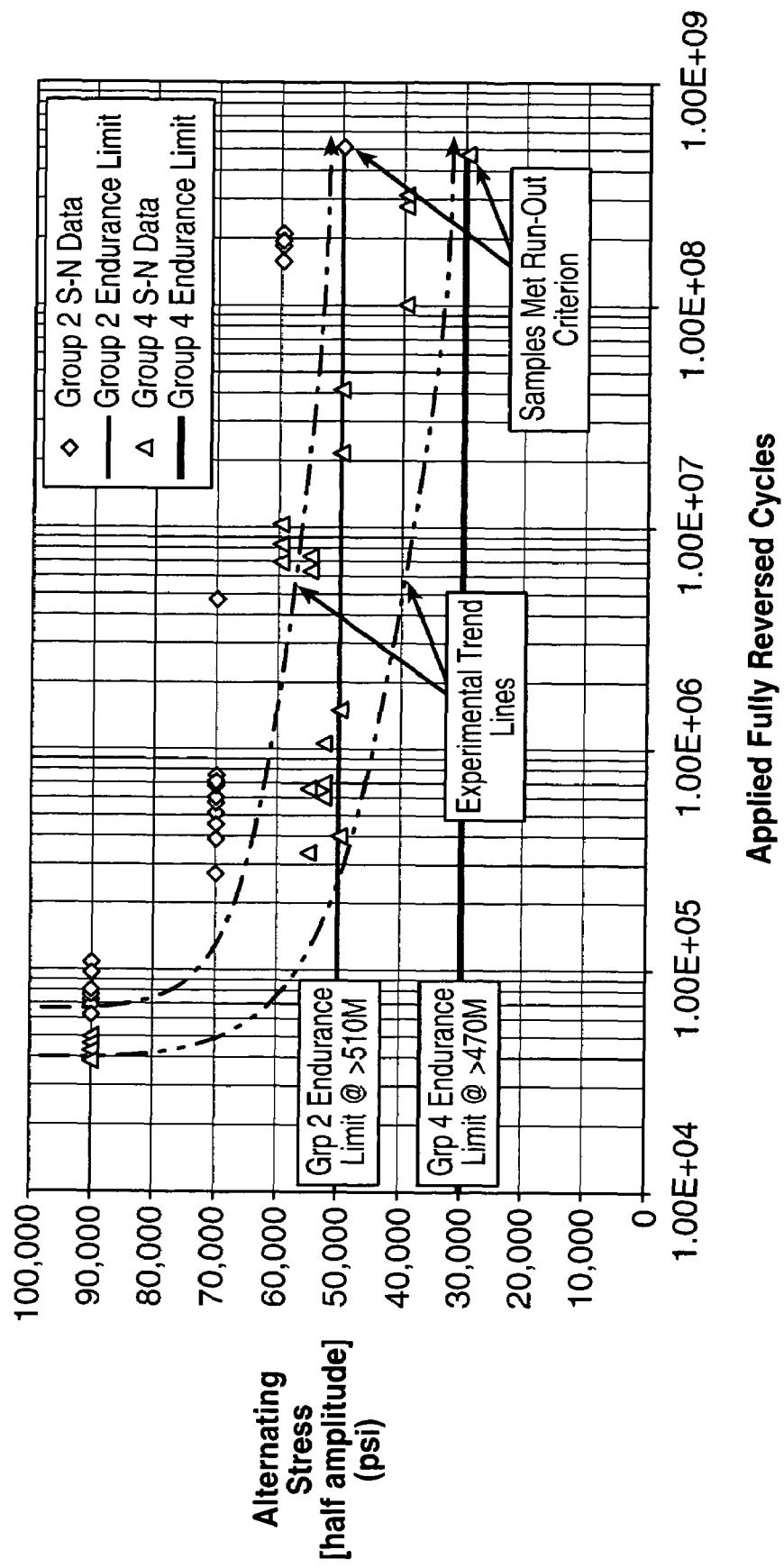
FIG. 2 is a graphical representation of the endurance limit chart as a function of thermomechanical processing for a cobalt-chromium alloy in accordance with the present invention.

More so, the effect of thermomechanical (TMP) on cyclic fatigue properties is on Co-based alloys, in accordance with the present invention, is reflected in FIG. 2. Examination of FIG. 2. shows the affect on fatigue strength (i.e. endurance limit) as a function of thermomechanical processing for the previously discussed TMP groups (2) and (4). TMP group (2) from this figure as utilized in this specific example shows a marked increase in the fatigue strength (i.e. endurance limit, the maximum stress below which a material can presumably endure an infinite number of stress cycles) over and against the TMP group (4) process.

The above-described alloy may be utilized in any number of implantable medical devices. The alloy is particularly advantageous in situations where magnetic resonance imaging is a useful diagnostic tool such as determining in-stent restenosis. Accordingly, although the alloy may be utilized for any implantable medical device, an exemplary stent constructed from the alloy is described below.

Figure 3:
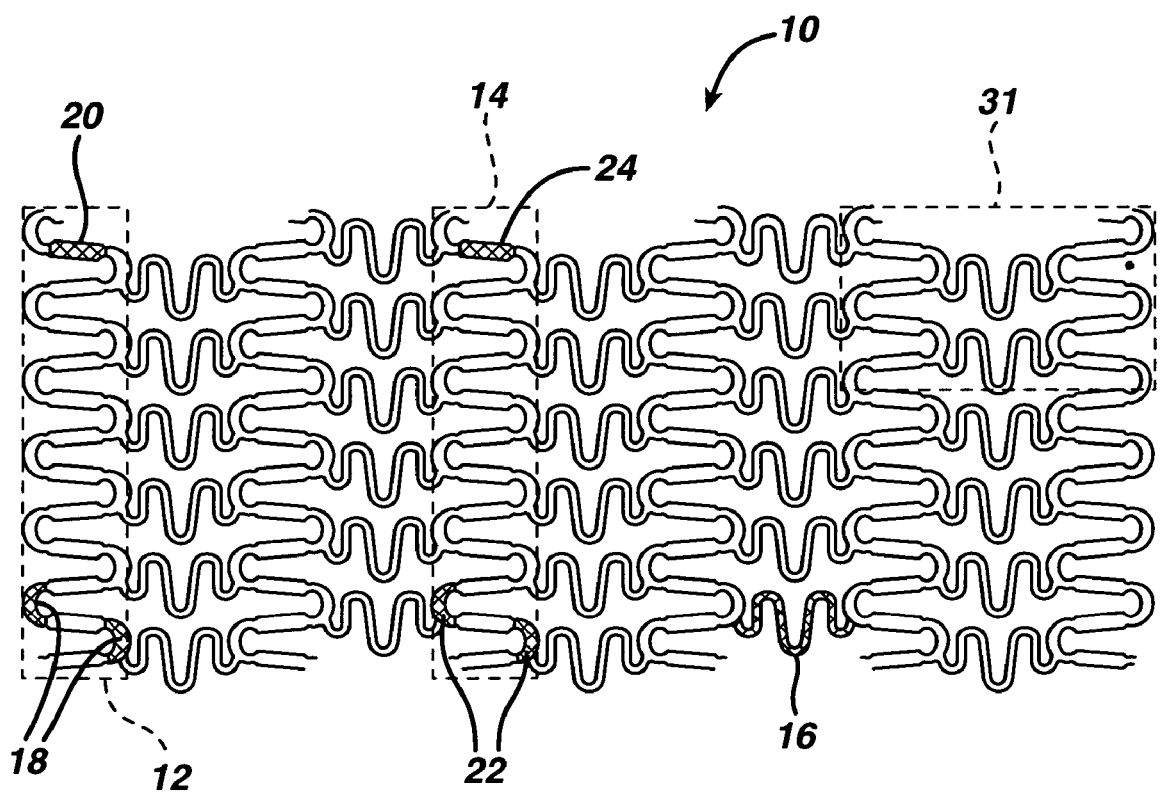
FIG. 3 is a flat layout diagrammatic representation of an exemplary stent fabricated from the biocompatible alloy in accordance with the present invention.

FIG. 3 is a flat layout of an exemplary embodiment of a stent that may be constructed utilizing the alloy of the present invention. The stent 10 comprises end sets of strut members 12 located at each end of the stent 10 and central sets of strut members 14 connected each to the other by sets of flexile "M" links 16. Each end set of strut members 12 comprises alternating curved sections 18 and diagonal sections 20 connected together to form a closed circumferential structure. The central sets of strut members 14 located longitudinally between the end sets of strut members 14 comprise curved sections 22 and diagonal sections 24 connected together to form a closed circumferential ring-like structure.

Figure 4:
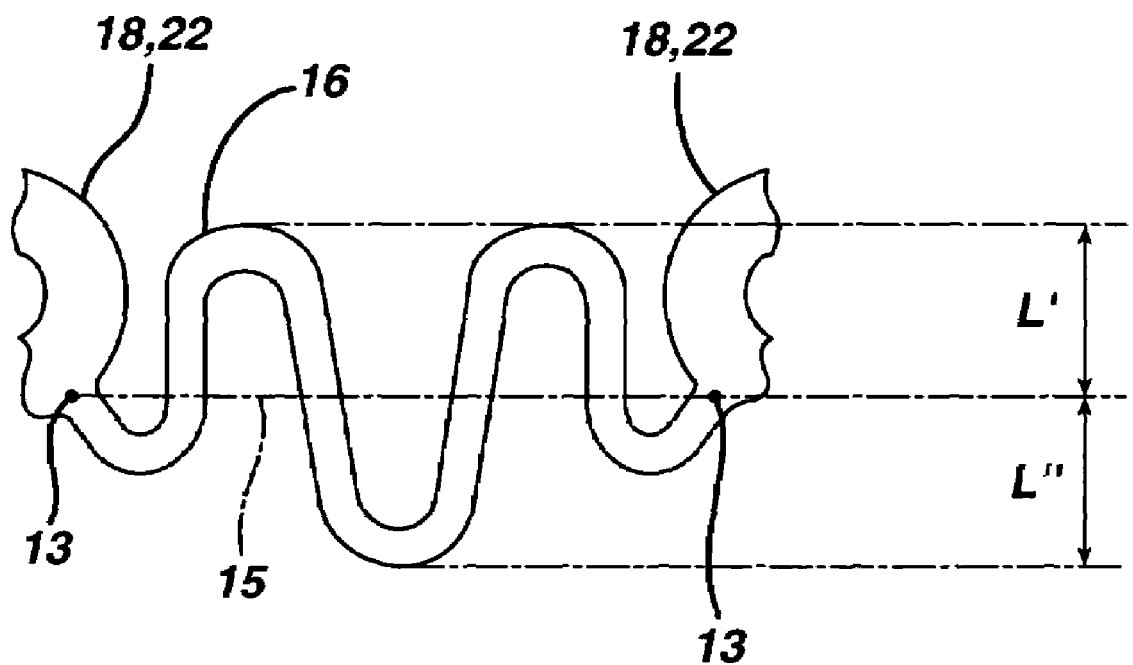
FIG. 4 is an enlarged view of the "M" links of the exemplary stent of FIG. 3 in accordance with the present invention.

Referring to FIG. 4 there is illustrated an enlargement of the flexible "M" links 16 of the stent 10. Each "M" link 16 has a circumferential extent, i.e. length, L' above and L" below line 11. The line 11 is drawn between the attachment points 13 where the "M" link 16 attaches to adjacent cured sections 18 or 22. Such a balanced design preferably diminishes any likelihood of the flexible connecting link 16 from expanding into the lumen of artery or other vessel.

As illustrated in FIG. 3, the diagonal sections 20 of the end sets of strut members 12 are shorter in length than the diagonal sections 24 of the central sets of strut members 14. The shorter diagonal sections 20 will preferably reduce the longitudinal length of metal at the end of the stent 10 to improve deliverability into a vessel of the human body. In the stent 10, the widths of the diagonal sections 20 and 24 are different from one another.

Figure 5:
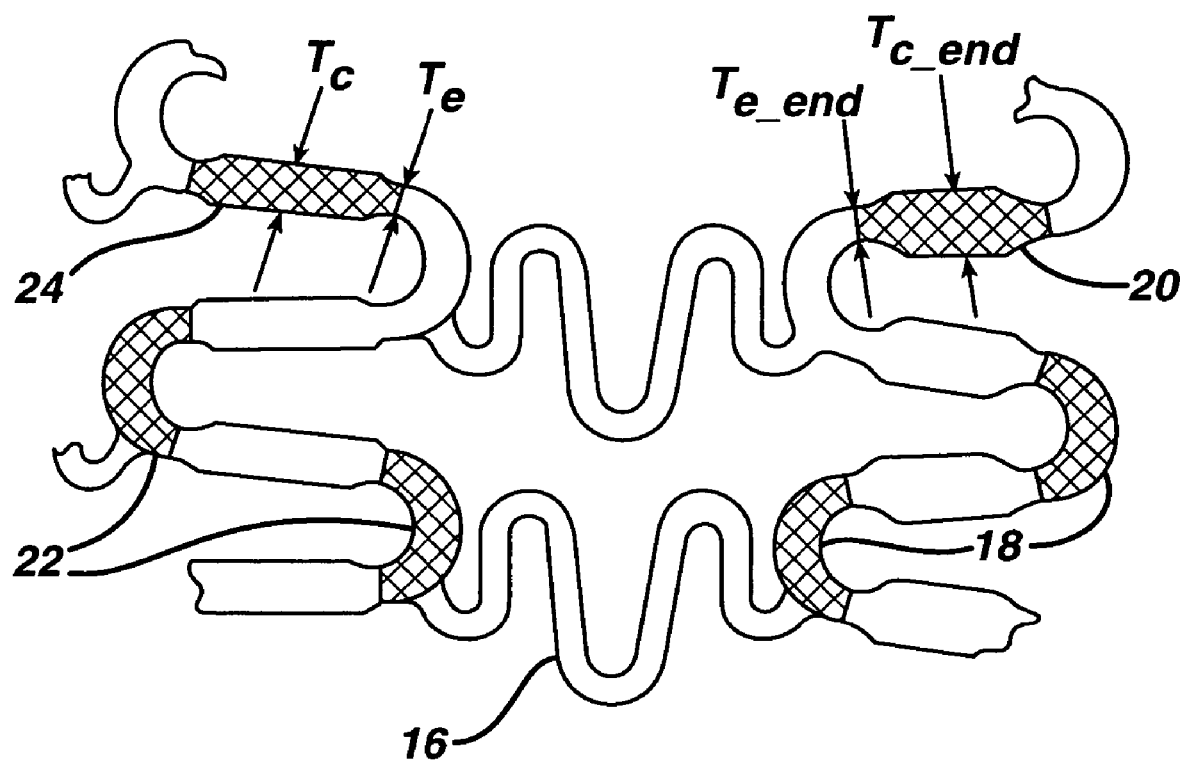
FIG. 5 is an enlarged view of a portion of the exemplary stent of FIG. 3 in accordance with the present invention.

Referring to FIG. 5, there is illustrated an expanded view of a stent section comprising an end set of strut members 12 and a central set of strut members 14. As illustrated, the diagonal sections 24 of the central sets of strut members 14 have a width at the center thereof, $T_c$, and a width at the end thereof, $T_e$, wherein $T_c$ is greater than $T_e$. This configuration allows for increased radiopacity without affecting the design of curved sections 22 that are the primary stent elements involved for stent expansion. In an exemplary embodiment, the curved sections 22 and 18 may be tapered and may have uniform widths with respect to one another as is explained in detail subsequently. The diagonal sections 20 of the end sets of strut members 12 also have a tapered shape. The diagonal sections 20 have a width in the center, $T_c$-end, and a width at the end, $T_e$-end, wherein $T_c$-end is greater than $T_e$-end. Because it is preferable for the end sets of strut members 12 to be the most radiopaque part of the stent 10, the diagonal section 20 center width $T_c$-end of the end sets of strut members 12 is wider than the width $T_c$ of the diagonal section 24. Generally, a wider piece of metal will be more radiopaque. Thus, the stent 10 has curved sections with a single bend connecting the diagonal sections of its sets of strut members, and flexible connecting links connecting the curved sections of its circumferential sets of strut members.

The width of the curved sections 22 and 18 taper down as one moves away from the center of the curve until a predetermined minimum width substantially equal to that of their respective diagonal sections 24 and 20. To achieve this taper, the inside arc of the curved sections 22 and 18 have a center that is longitudinally displaced from the center of the outside arc. This tapered shape for the curved sections 22 and 18 provides a significant reduction in metal strain with little effect on the radial strength of the expanded stent as compared to a stent having sets of strut members with a uniform strut width.

This reduced strain design has several advantages. First, it can allow the exemplary design to have a much greater usable range of radial expansion as compared to a stent with a uniform strut width. Second, it can allow the width at the center of the curve to be increased which increases radial strength without greatly increasing the metal strain (i.e. one can make a stronger stent). Finally, the taper reduces the amount of metal in the stent and that should improve the stent thrombogenicity.

The curved sections 18 of the end sets of strut members 12 and the curved sections 22 of the central sets of strut members 14 have the same widths. As a result of this design, the end sets of strut members 12, which have shorter diagonal sections 20, will reach the maximum allowable diameter at a level of strain that is greater than the level of strain experienced by the central sets of strut members 14.

It is important to note that although a stent is described, the alloy may be utilized for any number of implantable medical devices.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An implantable medical device being formed from an improved, magnetic resonance compatible low iron, cobalt chromium, solid-solution alloy comprising chromium in the range from about 19 weight percent to about 21 weight percent, tungsten in the range from about 14 weight percent to about 16 weight percent, nickel in the range from about 9 weight percent to about 11 weight percent, manganese in the range from about 1 weight percent to about 2 weight percent, carbon in the range from about 0.05 weight percent to about 0.15 weight percent, iron in an amount not to exceed 0.3 weight percent, silicon in an amount not to exceed 0.4 weight percent, phosphorus in an amount not to exceed 0.04 weight percent, sulfur in an amount not to exceed 0.03 weight percent and the remainder cobalt, the solid solution alloy being formed into a small diameter, thin-walled tube and machined into a lattice of interconnected elements each having a length, a width and a thickness defined as the distance between the inner and outer surfaces of the thin-walled tube, and wherein at least one of the elements at the end of the device having a width greater than the width of the elements at the center of the device.

2. The implantable medical device according to claim 1, wherein the solid-solution alloy is constructed through thermomechanical processing to exhibit relatively high strength and low ductility characteristics in the fully cold-worked state.

3. The implantable medical device according to claim 1, wherein the solid-solution alloy is constructed through thermomechanical processing to exhibit relatively moderate strength and moderate ductility characteristics in the partially cold-worked state.

4. The implantable medical device according to claim 3, wherein the solid-solution alloy is further constructed through age hardening for a predetermined time within a gaseous environment at a temperature less than the annealing temperature to precipitate one or more secondary phases, including at least one of intragranular and intergranular phases, from a substantially single phase structure.

5. The implantable medical device according to claim 4, wherein the age hardening temperature is in the range from about 750 degrees Fahrenheit to about 2,150 degrees Fahrenheit.

6. The implantable medical device according to claim 4, wherein the age hardening gaseous environment comprises hydrogen, nitrogen, argon and air.

7. The implantable medical device according to claim 3, wherein the solid-solution alloy is further constructed through stress relieving for a predetermined time within a gaseous environment at a temperature less than the annealing temperature while maintaining a substantially single phase to increase toughness and ductility.

8. The implantable medical device according to claim 7, wherein the stress relieving temperature is about or less than 100 degrees Fahrenheit below the annealing temperature.

9. The implantable medical device according to claim 7, wherein the stress relieving gaseous environment comprises hydrogen, nitrogen, argon and air.

10. The implantable medical device according to claim 3, wherein the solid-solution alloy is further constructed through stress relieving for a predetermined time with a vacuum environment at a temperature less than the annealing temperature while maintaining a substantially single phase to increase toughness and ductility.

11. The implantable medical device according to claim 10, wherein the stress relieving temperature is about or less than one hundred degrees Fahrenheit below the annealing temperature.

12. The implantable medical device according to claim 1, wherein the solid-solution alloy is constructed through thermomechanical processing to exhibit relatively low strength and high ductility characteristics in the fully annealed state.

13. The implantable medical device according to claim 1, wherein the medical device comprises a stent.

14. The implantable medical device according to claim 13, wherein the medical device comprises a vascular stent.

* * * * *